United States Patent
Ahn et al.

(10) Patent No.: US 9,018,439 B2
(45) Date of Patent: Apr. 28, 2015

(54) TRANSGENIC PIG IN WHICH HO-1 AND TNFR1-FC ARE SIMULTANEOUSLY EXPRESSED, AND METHOD FOR PRODUCING SAME

(75) Inventors: Curie Ahn, Gwacheon-si (KR); Byeong Chun Lee, Seoul (KR); Jong Ik Hwang, Seoul (KR); Jae Seok Yang, Seoul (KR); Goo Jang, Seoul (KR); Bum Rae Cho, Seoul (KR); Ok Jae Koo, Seoul (KR); Jung Taek Kang, Seoul (KR); Dae Kee Kwon, Seoul (KR)

(73) Assignee: Hanwha Advanced Materials Corporation, Seoul (KR)

( * ) Notice: Subject to any disclaimer, the term of this patent is extended or adjusted under 35 U.S.C. 154(b) by 238 days.

(21) Appl. No.: 13/520,056

(22) PCT Filed: Dec. 21, 2010

(86) PCT No.: PCT/KR2010/009172
§ 371 (c)(1),
(2), (4) Date: Jun. 29, 2012

(87) PCT Pub. No.: WO2011/081343
PCT Pub. Date: Jul. 7, 2011

(65) Prior Publication Data
US 2012/0278910 A1    Nov. 1, 2012

(30) Foreign Application Priority Data

Dec. 30, 2009 (KR) .................. 10-2009-0134548
Sep. 15, 2010 (KR) .................. 10-2010-0090543

(51) Int. Cl.
*A01K 67/027* (2006.01)
*C12N 15/00* (2006.01)
*C07K 14/715* (2006.01)
*C12N 9/02* (2006.01)
*C12N 15/85* (2006.01)

(52) U.S. Cl.
CPC ......... *C07K 14/7151* (2013.01); *A01K 67/0275* (2013.01); *A01K 2207/15* (2013.01); *A01K 2217/052* (2013.01); *A01K 2217/056* (2013.01); *A01K 2217/15* (2013.01); *A01K 2227/108* (2013.01); *A01K 2267/02* (2013.01); *A01K 2267/025* (2013.01); *C07K 2319/30* (2013.01); *C12N 9/0083* (2013.01); *C12N 15/8509* (2013.01); *C12N 2710/20051* (2013.01)

(58) Field of Classification Search
CPC ........... A61K 49/0008; C07K 2317/92; C07K 2319/32; C07K 2319/30; C07K 2319/74; A01K 2217/05; A01K 2267/025; A01K 2227/10; A01K 2227/105; A01K 2227/108; C12N 15/8509; C12N 15/62
See application file for complete search history.

(56) References Cited

U.S. PATENT DOCUMENTS

| 2004/0028658 A1 | 2/2004 | Faustman |
| 2005/0268347 A1 | 12/2005 | Tu et al. |
| 2009/0186097 A1 * | 7/2009 | Ayares .......................... 424/572 |

FOREIGN PATENT DOCUMENTS

| KR | 10-2007-0081531 A | 8/2007 |
| WO | 96/32478 A1 | 10/1996 |
| WO | 97/34631 A1 | 9/1997 |

OTHER PUBLICATIONS

Sabatine et al. Delayed Rejection of Soluble Tumor Necrosis Factor Receptor-Secreting Tumor Allografts.Transplantation, 1998, vol. 65, pp. 113-120.*
Garcia et al. High sensitivity of transgenic mice expressing soluble TNFRI fusion protein to mycobacterial infections: synergistic action of TNF and IFN-y in the differentiation of protective granulomas. European J. Immunology, 1997, vol. 27, pp. 3182-3190.*
Machen, Jr. et al. Gene Therapy vol. 11, pp. 1506-1514 (2004).
Lee, G. S. et al., Theriogenology vol. 63, pp. 973-991 (2005).
Laumonier, T. et al., Molecular Therapy vol. 16, No. 2, pp. 404-410 (2008).
Blames et al., Diabetes vol. 51, pp. 66-72 (2002).
Rosenblum MG, et al., Cancer. Immunol. Immunother., vol. 40, No. 5, pp. 322-328 (1995).
Jorgensen C. et al., Immunology vol. 93, No. 4, pp. 518-523 (1998).
Nagy T. et al., APMIS vol. 107, No. 10, pp. 903-912 (1999).
Benda B. et al., Xenotransplantation vol. 7, No. 3, pp. 206-213 (2000).
Kirkiles-Smith NC. et al., J. Immunol., vol. 164, No. 12, pp. 6601-6609 (2000).
Tatham et al., Hum. Reprod. vol. 11, No. 7, pp. 1499-1503 (1996).

* cited by examiner

*Primary Examiner* — Deborah Crouch
(74) *Attorney, Agent, or Firm* — McDonnell Boehnen Hulbert & Berghoff LLP

(57) ABSTRACT

The present invention relates to a method for producing a transgenic pig in which immune rejection response is inhibited, and in which human HO-1 genes and TNFR1-Fe fusion genes are simultaneously expressed. The present invention also relates to a transgenic pig for organ transplantation, which is produced by the method, and in which immune rejection response is inhibited. The present invention also relates to a somatic-cell-donating cell strain for producing the transgenic pig, and to a method for producing organs, from the transgenic pig, in which the immune rejection response is inhibited.

17 Claims, 11 Drawing Sheets

FIG. 2

```
ATGGAGCGTCCGCAACCCGACAGCATGCCCCAGGATTTGTCAGAGGCCCTGAAGGAGGCC
 M  E  R  P  Q  P  D  S  M  P  Q  D  L  S  E  A  L  K  E  A
ACCAAGGAGGTGCACACCCAGGCAGAGAATGCTGAGTTCATGAGGAACTTTCAGAAGGGC
 T  K  E  V  H  T  Q  A  E  N  A  E  F  M  R  N  F  Q  K  G
CAGGTGACCCGAGACGGCTTCAAGCTGGTGATGGCCTCCCTGTACCACATCTATGTGGCC
 Q  V  T  R  D  G  F  K  L  V  M  A  S  L  Y  H  I  Y  V  A
CTGGAGGAGGAGATTGAGCGCAACAAGGAGAGCCCAGTCTTTGCCCCTGTCTACTTCCCA
 L  E  E  E  I  E  R  N  K  E  S  P  V  F  A  P  V  Y  F  P
GAAGAGCTGCACCGGAAGGCTGCCCTGGAGCAGGACCTGGCCTTCTGGTACGGGCCCCGC
 E  E  L  H  R  K  A  A  L  E  Q  D  L  A  F  W  Y  G  P  R
TGGCAGGAGGTCATCCCCTACACACCCAGCCATGCAGCGCTATGTGAAGCGGCTCCACGAG
 W  Q  E  V  I  P  Y  T  P  A  M  Q  R  Y  V  K  R  L  H  E
GTGGGCCACACAGAGCCCGAGCTGCTGGTGGCCCACGCCTACACCCGCTACCTGGGTGAC
 V  G  H  T  E  P  E  L  L  V  A  H  A  Y  T  R  Y  L  G  D
CTGTCTGGGGGCCAGGTGCTCAAAAAGATTGCCCAGAAAGCCCTGGACCTGCCCAGCTCT
 L  S  G  G  Q  V  L  K  K  I  A  Q  K  A  L  D  L  P  S  S
GGGGAGGGCCTGGCCTTCTTCACCTTCCCCAACATTGCCAGTGCCACCAAGTTCAAGCAG
 G  E  G  L  A  F  F  T  F  P  N  I  A  S  A  T  K  F  K  Q
CTCTACCGCTCCCGCATGAACTCCCTGGAGATGACTCCCGCAGTCAGGCAGAGGGTGATA
 L  Y  R  S  R  M  N  S  L  E  M  T  P  A  V  R  Q  R  V  I
GAAGAGGCCAAGACTGCCTTCCTGCTCAACATCCAGCTCTTTGAGGAGTTGCAGGAGCTG
 E  E  A  K  T  A  F  L  L  N  I  Q  L  F  E  E  L  Q  E  L
CTGACCCATGACACCAAGGACCAGAGCCCCTCACGGGCACCAGGGTTGCGCCAGCGCGCC
 L  T  H  D  T  K  D  Q  S  P  S  R  A  P  G  L  R  Q  R  A
AGCAACAAAGTGCAAGATTCTGCCCCCGTGGAGACTCCCAGAGGGAAGCCCCCACTCAAC
 S  N  K  V  Q  D  S  A  P  V  E  T  P  R  G  K  P  P  L  N
ACCCGCTCCCAGGCTCCGCTTCTCCGATGGGTCCTTACACTCAGCTTTCTGGTGGCCACA
 T  R  S  Q  A  P  L  L  R  W  V  L  T  L  S  F  L  V  A  T
GTTGCTGTAGGCCTTTATGCCATGTGA (SEQ ID NO: 1)
 V  A  V  G  L  Y  A  M  *
```

FIG. 5

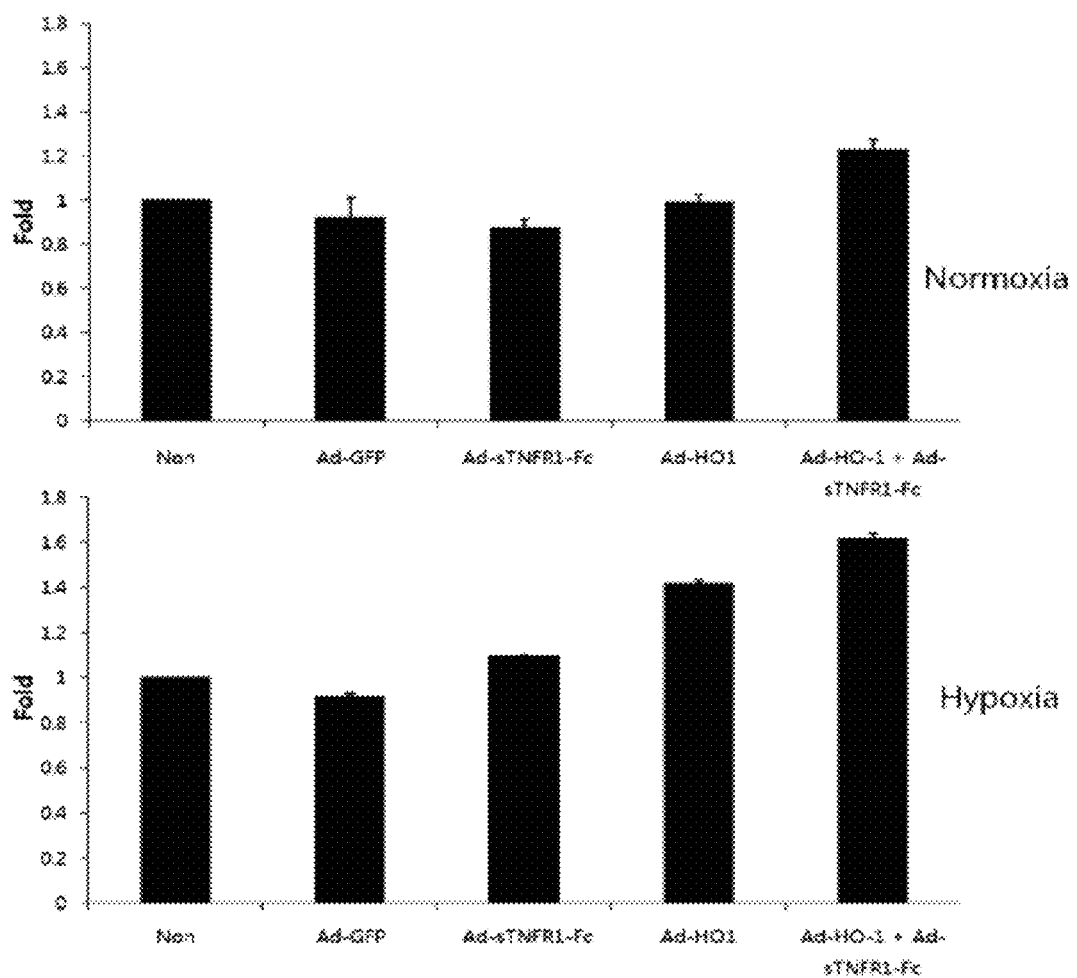

SEQUENCE LISTING

```
<160> NUMBER OF SEQ ID NOS: 9

<210> SEQ ID NO 1
<211> LENGTH: 867
<212> TYPE: DNA
<213> ORGANISM: Homo sapiens

<400> SEQUENCE: 1
atggagcgtc cgcaacccga cagcatgccc caggatttgt cagaggccct gaaggaggcc      60
accaaggagg tgcacaccca ggcagagaat gctgagttca tgaggaactt tcagaagggc     120
caggtgaccc gagacggctt caagctggtg atggcctccc tgtaccacat ctatgtggcc     180
ctggaggagg agattgagcg caacaaggag agcccagtct tcgccctgt ctacttccca      240 gaagagctga accgcaaggc tgccctggag caggacctgg ccttctggta cgggccccgc     300
tggcaggagg tcatccccta cacaccagcc atgcagcgct atgtgaagcg gctccacgag     360
gtggggcgca cagagcccga gctgctggtg gcccacgcct acacccgcta cctgggtgac     420
ctgtctgggg gccaggtgct caaaaagatt gcccagaaag ccctggacct gcccagctct     480
ggcgagggcc tggccttctt caccttcccc aacattgcca gtgccaccaa gttcaagcag     540
ctctaccgct cccgcatgaa ctccctggag atgactcccg cagtcaggca gagggtgata     600
gaagaggcca agactgcgtt cctgctcaac atccagctct ttgaggagtt gcaggagctg     660
ctgacccatg acaccaagga ccagagcccc tcacgggcac cagggcttcg ccagcgggcc     720
agcaacaaag tgcaagattc tgcccccgtg gagactccca gagggaagcc cccactcaac     780
acccgctccc aggctccgct tctccgatgg gtccttacac tcagctttct ggtggcgaca     840
gttgctgtag ggctttatgc catgtga                                         867

<210> SEQ ID NO 2
<211> LENGTH: 33
<212> TYPE: DNA
<213> ORGANISM: Artificial Sequence
<220> FEATURE:
<223> OTHER INFORMATION: Forward primer for HO-1

<400> SEQUENCE: 2
cgggctagca ccatggagcg tccgcaaccc gac                                    33

<210> SEQ ID NO 3
<211> LENGTH: 30
<212> TYPE: DNA
```

<213> ORGANISM: Artificial Sequence
<220> FEATURE:
<223> OTHER INFORMATION: Reverse primer for HO-1

<400> SEQUENCE: 3
cgggaattct cacatggcat aaagccctac         30

<210> SEQ ID NO 4
<211> LENGTH: 27
<212> TYPE: DNA
<213> ORGANISM: Artificial Sequence
<220> FEATURE:
<223> OTHER INFORMATION: Forward primer for sTNFR1

<400> SEQUENCE: 4
ataagcttat gggcctctcc accgtgc            27

<210> SEQ ID NO 5
<211> LENGTH: 22
<212> TYPE: DNA
<213> ORGANISM: Artificial Sequence
<220> FEATURE:
<223> OTHER INFORMATION: Reverse primer for sTNFR1

<400> SEQUENCE: 5
tgtggtgcct gagtcctcag tg                 22

<210> SEQ ID NO 6
<211> LENGTH: 23
<212> TYPE: DNA
<213> ORGANISM: Artificial Sequence
<220> FEATURE:
<223> OTHER INFORMATION: Foward primer for human IgG-Fc

<400> SEQUENCE: 6
acatgcccac cgtgcccagc acc                23

<210> SEQ ID NO 7
<211> LENGTH: 28
<212> TYPE: DNA
<213> ORGANISM: Artificial Sequence
<220> FEATURE:
<223> OTHER INFORMATION: Reverse primer for human IgG-Fc

<400> SEQUENCE: 7
atctcgagtc atttacccgg agacaggg           28

<210> SEQ ID NO 8
<211> LENGTH: 1305
<212> TYPE: DNA
<213> ORGANISM: Artificial Sequence
<220> FEATURE:
<223> OTHER INFORMATION: Human sTNFR1-Fc

<400> SEQUENCE: 8
atgggcctct ccaccgtgcc tgacctgctg ctgccactgg tgctcctgga gctgttggtg      60
ggaatatacc cctcaggggt tattggactg gtccctcacc taggggacag ggagaagaga     120
gatagtgtgt gtccccaagg aaaatatatc caccctcaaa ataattcgat ttgctgtacc     180
aagtgccaca aggaaccta cttgtacaat gactgtccag gcccggggca ggatacggac     240
tgcagggagt gtgagagcgg ctccttcacc gcttcagaaa accacctcag acactgcctc     300
agctgctcca atgccgaaa ggaaatgggt caggtgagaa tctcttcttg cacagtggac     360
cgggacaccg tgtgtggctg caggaagaac cagtaccggc attattggag tgaaaacctt     420

```
ttccagtgct tcaattgcag cctctgcctc aatgggaccg tgcacctctc ctgccaggag      480
aaacagaaca ccgtgtgcac ctgccatgca ggtttctttc taagagaaaa cgagtgtgtc      540
tcctgtagta actgtaagaa aagcctggag tgcacgaagt tgtgcctacc ccagattgag      600
aatgttaagg gcactgagga ctcaggcacc acaacatgcc caccgtgccc agcacctgaa      660
ctcctggggg gaccgtcagt cttcctcttc cccccaaaac ccaaggacac cctcatgatc      720
tcccggaccc ctgaggtcac atgcgtggtg gtggacgtga gccacgaaga ccctgaggtc      780
aagttcaact ggtacgtgga cggcgtggag gtgcataatg ccaagacaaa gccgcgggag      840
gagcagtaca acagcacgta ccgtgtggtc agcgtcctca ccgtcctgca ccaggactgg      900
ctgaatggca aggagtacaa gtgcaaggtc tccaacaaag ccctcccagc ccccatcgag      960
aaaaccatct ccaaagccaa agggcagccc cgagaaccac aggtgtacac cctgccccca     1020
tcccgggatg agctgaccaa gaaccaggtc agcctgacct gcctggtcaa aggcttctat     1080
cccagcgaca tcgccgtgga gtgggagagc aatgggcagc cggagaacaa ctacaagacc     1140
acgcctcccg tgctggactc cgacggcccc ttcttcctct acagcaagct caccgtggac     1200
aagagcaggt ggcagcaggg gaacgtcttc tcatgctccg tgatgcatga ggctctgcac     1260
aaccactaca cgcagaagag cctctccctg tctccgggta aatga                     1305
```

```
<210> SEQ ID NO 9
<211> LENGTH: 18
<212> TYPE: DNA
<213> ORGANISM: Artificial Sequence
<220> FEATURE:
<223> OTHER INFORMATION: Reverse primer for HO-1

<400> SEQUENCE: 9
aaggtgaaga aggccagg                                                      18
```

TRANSGENIC PIG IN WHICH HO-1 AND TNFR1-FC ARE SIMULTANEOUSLY EXPRESSED, AND METHOD FOR PRODUCING SAME

BACKGROUND OF THE INVENTION

1. Field of the Invention

The present invention relates to a method for producing a transgenic pig suppressed in immune rejection response in which a gene coding for human HO-1 protein and a gene coding for TNFR1-Fc fusion protein are expressed simultaneously. More particularly, the present invention relates to a method for producing a transgenic pig suppressed in immune rejection response, comprising a) isolating somatic cells from a pig; b) introducing a gene coding for human HO-1 (Heme oxygenase-1) protein and a gene coding for human TNFR1-Fc (Tumor necrosis factor receptor 1-Fc) fusion protein into the somatic cells; c) selecting and culturing the somatic cells that are introduced with the genes; d) removing the nucleus from an oocyte of the pig and fusing it with the selected somatic cell to prepare a somatic cell nuclear transferred embryo; and e) implanting the embryo. The present invention also relates to a transgenic pig suppressed in immune rejection response for organ transplantation that is produced by the above method, a somatic donor cell line for producing the transgenic pig, and a method for producing transplantable organ suppressed in immune rejection response from the transgenic pig.

2. Description of the Related Art

Pancreatic islet (hereinafter referred to as "islet") transplantation is an innovative treatment strategy for diabetes. However, an explosive increase in the number of diabetic patients causes the severe lack of donor islets. Organ transplantation is the procedure of replacing diseased organs or parts of organs with healthy organs of another person when diseased organs lose their functions and drugs no longer help to treat the disease, and commonly includes transplantation of organs from living persons. Therefore, many attempts have been made to address the problem of the lack of donor islets due to the explosive increase in the number of diabetic patients. An example thereof includes stem cell xenotransplants, which is a therapeutic method of replacing damaged cells with stem cells that are differentiated and proliferated as much as needed. However, it has a limitation that the stem cells cannot be developed into an organ consisting of different types of cells. Therefore, xenotransplantation is used for direct replacement of organs when needed.

One of the promising alternative ways for human organs is islet xenotransplantation using animals capable of providing a sufficient quantity of donor islets, and many animals such as monkeys and pigs are attempted to be used to supply organs for xenotransplantation. Among them, pigs have numerous similarities with humans in terms of the anatomy and physiology, and their organs are similar in size to humans. In addition, pigs are easy to breed, and they have a short gestation period (112 days) and large litters (6-12 piglets). Owing to these advantages, the use of pig islet cells has been actively studied.

When islets are isolated for islet transplantation, they are cultured in vitro for a predetermined time prior to transplantation. However, if oxidative stress and other cell damages occur in islet cells during the isolation procedure, cell death is induced during in vitro cultivation of islet cells. Thus, the protection of insulin secreting cells from oxidative stress is thus regarded as a potential approach to prevent early graft failure of transplanted islets (Biarnes et al., *Diabetes*, 2002; 51: 66-72.). Because the inflammatory responses after islet transplantation might reduce a survival rate of implanted islet, it is also very important to control the inflammatory responses.

HO-1 (Heme oxygenase-1) is an enzyme that finally degrades heme into bilirubin and $Fe^{2+}$, and is an antioxidant enzyme capable of cytoprotection via radical scavenging or apoptosis prevention.

TNF-α is a representative inflammatory cytokine, and a mediator that is mainly expressed in monocytes/macrophages and natural killer cells to induce inflammation. Many previous studies reported that TNF-α is one of the causes inducing immune rejection responses in xenotransplantation as well as allotransplantation (Carel J C. et al., *Transplantation*, 1993, 55(2):456-458; Rosenblum M G. et al., *Cancer. Immunol. Immunother.*, 1995, 40(5):322-328; Lin Y. et al., *Transplantation*, 1997, 64(12):1677-1683; Lin H. et al., J. Surg. Res, 1997, 72(1):84-88; Jorgensen C. et al., *Immunology*, 1998, 93(4):518-523; Nagy T. et al., APMIS, 1999, 107(10):903-912; Benda B et al., *Xenotransplantation*, 2000, 7(3):206-213; Kirkiles-Smith N C. et al., *J. Immunol.*, 2000, 164(12): 6601-6609).

However, there was no technical idea that a gene coding for human HO-1 protein and a gene coding for TNFR1-Fc fusion protein capable of inhibiting human TNF-α are co-transfected into a pig to produce a transgenic pig, so as to protect islet cells from oxidative stress upon isolation and inflammatory responses after transplantation, thereby increasing the success rate of transplantation.

The present inventors have made many efforts to develop a method for suppressing immune rejection response and protecting islet cells from oxidative stress and inflammatory responses after transplantation. As a result, they have developed a porcine cell that is introduced with a gene coding for human HO-1 protein and a gene coding for TNFR1-Fc fusion protein composed of the extracellular region of human TNFR1 fused to IgG Fc region, and a method for producing a transgenic pig by nuclear transfer using the cell as a donor cell, thereby completing the present invention.

SUMMARY OF THE INVENTION

An object of the present invention is to provide a method for producing a transgenic pig suppressed in immune rejection response that is introduced with a gene coding for human HO-1 (Heme oxygenase-1) protein and a gene coding for human TNFR1-Fc (Tumor necrosis factor receptor 1-Fc) fusion protein.

Another object of the present invention is to provide a transgenic pig suppressed in immune rejection response that is produced by the above method.

Still another object of the present invention is to provide a somatic donor cell line for the production of the transgenic pig.

Still another object of the present invention is to provide a method for producing transplantable organs suppressed in immune rejection response, comprising producing the transgenic pig by the above method; and isolating the organ from the transgenic pig.

BRIEF DESCRIPTION OF THE DRAWINGS

FIG. 2 shows nucleotide and amino acid sequences of the gene coding for human HO-1 protein;

FIG. 5 shows nucleotide and amino acid sequences of the gene coding for human sTNFR1-Fc fusion protein;

FIG. 12 shows the result of MTT assay after transfection of newborn pig islet cells with GFP, sTNFR1-Fc, and HO-1-expressing adenoviruses and cultivation under normoxic and hypoxic conditions.

DETAILED DESCRIPTION OF THE PREFERRED EMBODIMENTS

Figure 1:
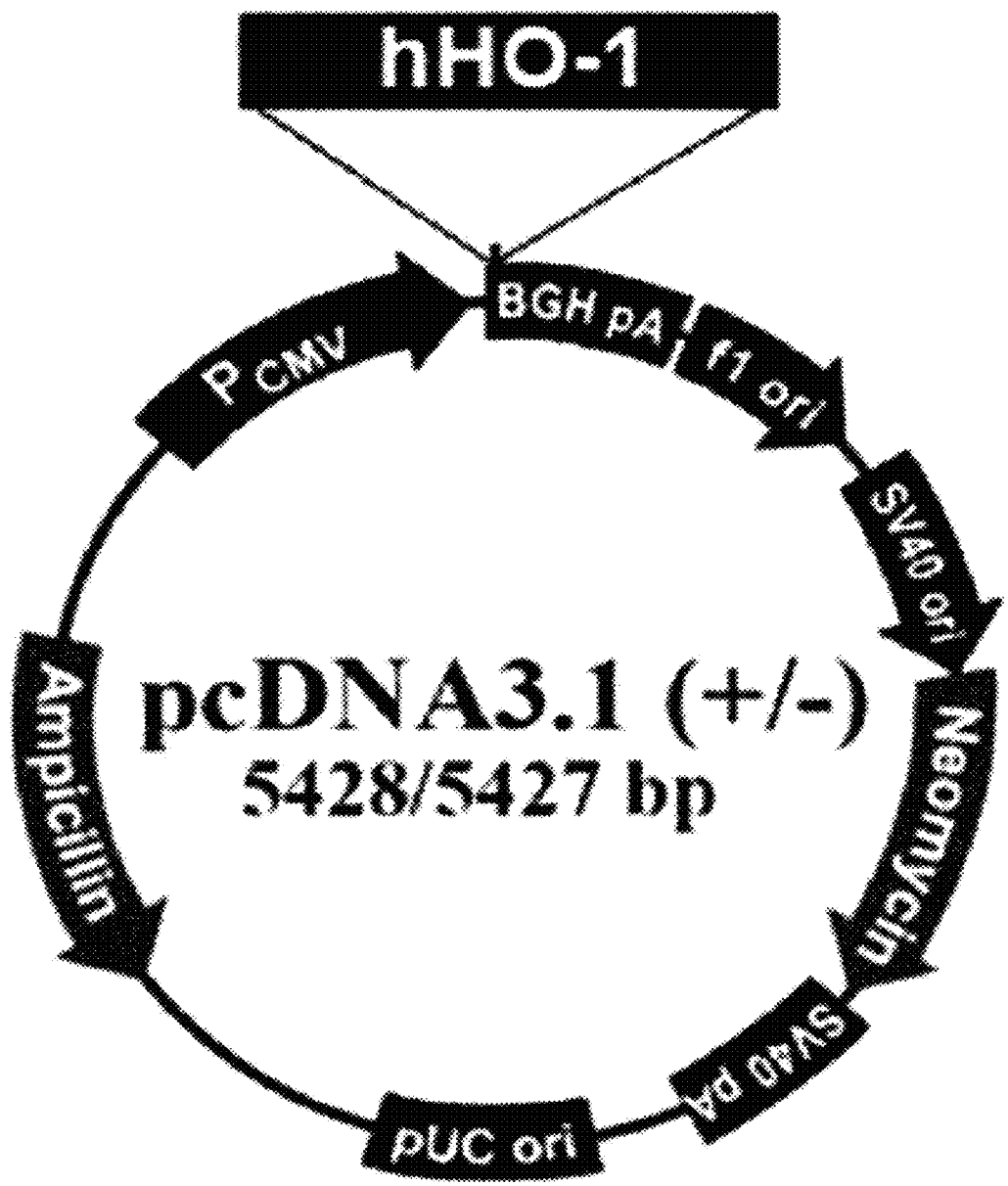
FIG. 1 is a schematic view of a cleavage map of a gene coding for human HO-1 protein-inserted expression vector.

In one aspect to achieve the above objects, the present invention relates to a method for producing a transgenic pig suppressed in immune rejection response, comprising a) isolating somatic cells from a pig; b) introducing a gene coding for human HO-1 (Heme oxygenase-1) protein and a gene coding for human TNFR1-Fc (Tumor necrosis factor receptor 1-Fc) fusion protein into the somatic cells; c) selecting and culturing the somatic cells that are introduced with the genes; d) removing the nucleus from an oocyte of the pig and fusing it with the selected somatic cell to prepare a somatic cell nuclear transferred embryo; and e) implanting the embryo.

As used herein, the term "a gene coding for HO-1 (Heme oxygenase-1) protein" means a gene encoding an enzyme that is expressed in cells by a variety of stress such as heavy metals, endotoxin, ultraviolet, heat shock, reactive oxygen, hypoxia, and the like. HO-1 is an enzyme that finally degrades heme into bilirubin and $Fe^{2+}$, and is an antioxidant enzyme capable of cytoprotection via radical scavenging or apoptosis prevention and improving functions of the transplanted islet. In the present invention, HO-1 inhibits proliferation of CD4+ T– cells and activates proliferation of endothelial cells at the same time, thereby normalizing immune cells in the body. Consequently, immune rejection responses to xenotransplantation can be suppressed, and islet cells show resistance to oxidative stress when isolated and are protected via apoptosis prevention.

Preferably, the sequence of the gene coding for human HO-1 protein can be obtained from the known gene database. Any sequence may be used without limitation, as long as it is introduced into porcine somatic cells to show HO-1 functions. Preferably, the gene coding for human HO-1 protein represented by SEQ ID NO: 1 may be used.

As used herein, the term "a gene coding for TNFR1-Fc (Tumor necrosis factor receptor 1-Fc) fusion protein" means a fusion protein of the immunoglobulin Fc region and the extracellular domain of TNFR1, which is able to bind with TNF-α. As used herein, the terms "the gene coding for TNFR1-Fc fusion protein" and "the gene coding for TNFR1-Fc protein" are interchangeably used. In the present invention, any type of TNFR1-Fc protein may be used without limitation, as long as it is able to bind with TNF-α and inhibit TNF-α. Preferably, a fusion protein of soluble tumor necrosis factor receptor 1 (soluble TNFR1, sTNFR1) and immunoglobulin Fc region may be used.

As used herein, the term "immunoglobulin Fc region" refers to the heavy-chain constant region 2 ($C_H2$) and the heavy-chain constant region 3 ($C_H3$) of an immunoglobulin, except for the variable regions of the heavy and light chains, the heavy-chain constant region 1 ($C_H1$) and the light-chain constant region 1 ($C_L1$) of the immunoglobulin. Also, the immunoglobulin Fc region of the present invention may contain a part or all of the Fc region comprising the heavy-chain constant region 1 ($C_H1$) and/or the light-chain constant region 1 ($C_L1$), except for the variable regions of the heavy and light chains, as long as it has effects similar to or better than the native protein. Also, the Ig Fc region may be a fragment having a deletion in a relatively long portion of the amino acid sequence of $C_H2$ and/or $C_H3$. That is, the immunoglobulin Fc region of the present invention may include 1) a $C_H1$ domain, a $C_H2$ domain, a $C_H3$ domain and a $C_H4$ domain, 2) a $C_H1$ domain and a $C_H2$ domain, 3) a $C_H1$ domain and a $C_H3$ domain, 4) a $C_H2$ domain and a $C_H3$ domain, 5) a combination of one or more domains and an immunoglobulin hinge region (or a portion of the hinge region), and 6) a dimer of each domain of the heavy-chain constant regions and the light-chain constant region. The immunoglobulin Fc region of the present invention includes a native amino acid sequence, and a sequence derivative (mutant) thereof. An amino acid sequence derivative is a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification. Also, other various derivatives are possible, including one in which a region capable of forming a disulfide bond is deleted, or certain amino acid residues are eliminated at the N-terminus of a native Fc form or a methionine residue is added thereto. Further, to remove effector functions, a deletion may occur in a complement-binding site, such as a C1q-binding site and an ADCC site. Techniques of preparing such sequence derivatives of the immunoglobulin Fc region are disclosed in the International Patent Publication Nos. WO 97/34631 and WO 96/32478. Amino acid exchanges in proteins and peptides, which do not generally alter the activity of molecules, are known in the art. The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly in both directions. The Fc region, if desired, may be modified by phosphorylation, sulfation, acrylation, glycosylation, methylation, farnesylation, acetylation, amidation, and the like. The aforementioned Fc derivatives are derivatives that have a biological activity identical to the Fc region of the present invention or improved structural stability, for example, against heat, pH, or the like.

On the other hand, the immunoglobulin Fc region may be derived from humans or other animals including cows, goats, swine, mice, rabbits, hamsters, rats and guinea pigs, and preferably humans. In addition, the immunoglobulin Fc region may be an Fc region that is derived from IgG, IgA, IgD, IgE and IgM, or that is made by combinations thereof or hybrids thereof. Preferably, it is derived from IgG or IgM, which is among the most abundant proteins in human blood, and most preferably from IgG, which is known to enhance the half-lives of ligand-binding proteins.

On the other hand, the term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The term "hybrid", as used herein, means that sequences encoding two or more immunoglobulin Fc regions of different origin are present in a single-chain immunoglobulin Fc region. In the present invention, various types of hybrids are possible. That is, domain hybrids may be composed of one to four domains selected from the group consisting of $C_H1$, $C_H2$, $C_H3$ and $C_H4$ of IgG Fc, IgM Fc, IgA Fc, IgE Fc and IgD Fc, and may include the hinge region. On the other hand, IgG is divided into IgG1, IgG2, IgG3 and IgG4 subclasses, and the present invention includes combinations and hybrids thereof.

As used herein, the fusion protein of soluble cytokine receptor and immunoglobulin (hereinafter, referred to as 'Ig') has the following advantages over a monomer of the intrinsic molecule or a molecule not fused to Ig:

1) the fusion protein has increased total avidity to a ligand because it has bivalency in a dimer form;
2) the fusion protein is present in an undestroyed form in serum for a longer period of time by virtue of increased molecular stability;
3) effector cells are activated by the Fc (Fragment crystallizable) portion of the immunoglobulin heavy chain; and
4) the fusion protein is isolated and purified by a convenient method [e.g., isolation and purification using protein A].

The fusion protein of the present invention is manufactured in a form excluding $C_H1$ domain of the heavy chain, resulting in a dimer form that does not bind with the light chain of immunoglobulin.

Preferably, the sequences of the gene coding for human TNFR1 protein and Fc may be obtained from the known database, respectively. Any sequence may be used without limitation, as long as it is introduced into porcine somatic cells to show the functions of TNFR1-Fc fusion protein, and preferably the gene coding for TNFR1-Fc fusion protein represented by SEQ ID NO: 8.

As used herein, the term "transgenic pig" means a pig that is genetically modified by artificial insertion of a foreign piece of gene into the porcine genome. The preferred animal is a pig, but the method of the present invention may be applied to mammals in nature capable of providing humans with their organs, so as to produce transgenic animals suppressed in immune rejection response.

In one preferred embodiment, the somatic cells isolated from the pig may be fetal or adult somatic cells of a pig without limitation, in step a) of isolating somatic cells from the pig. If the fetal pig is used, it is preferably at day 20 to 40 of gestation, and more preferably at day 25 to 35 of gestation. In one specific Example of the present invention, the fetal pig at day 25 to 35 of gestation was used to isolate porcine somatic cells. For isolation of the somatic cells, the known method may be used without limitation. In one specific Example of the present invention, the skin on the back of the fetal pig was isolated using a scalpel blade to obtain fibroblasts.

In one preferred embodiment, in step b) of introducing a gene coding for human HO-1 protein and a gene coding for human TNFR1-Fc fusion protein into the somatic cells, the gene coding for human HO-1 protein may be preferably a gene represented by SEQ ID NO: 1, and the gene coding for human TNFR1-Fc fusion protein may be preferably a gene represented by SEQ ID NO: 8.

In one preferred embodiment, the method of introducing the gene coding for human HO-1 protein and the gene coding for human TNFR1-Fc fusion protein of step b) may be performed to introduce an expression vector including the gene, or to increase the copy number of the corresponding gene in the genome, or to introduce or overexpress the corresponding gene by substitution or modification of its promoter sequence.

The method of transfecting the gene into cells may be performed by a biochemical method, a physical method or a virus-mediated transfection method. Preferably, the biochemical method is performed using FuGene6 (Roche, USA), Lipofectamine (Lipofectamine™2000, Invitrogen, USA) or ExGen 500 (MBI Fermentas International Inc. CANADA), and more preferably, lipid-mediated transfection using Lipofectamine. In addition, the expression vector comprising the gene may be any expression vector that can be expressed in porcine somatic cell lines. In the specific Example of the present invention, a pcDNA 3.1 vector was used as the expression vector comprising the gene coding for human HO-1 protein, and a pcDNA6 vector was used as the expression vector comprising the gene coding for human TNFR1-Fc fusion protein.

Figure 3:
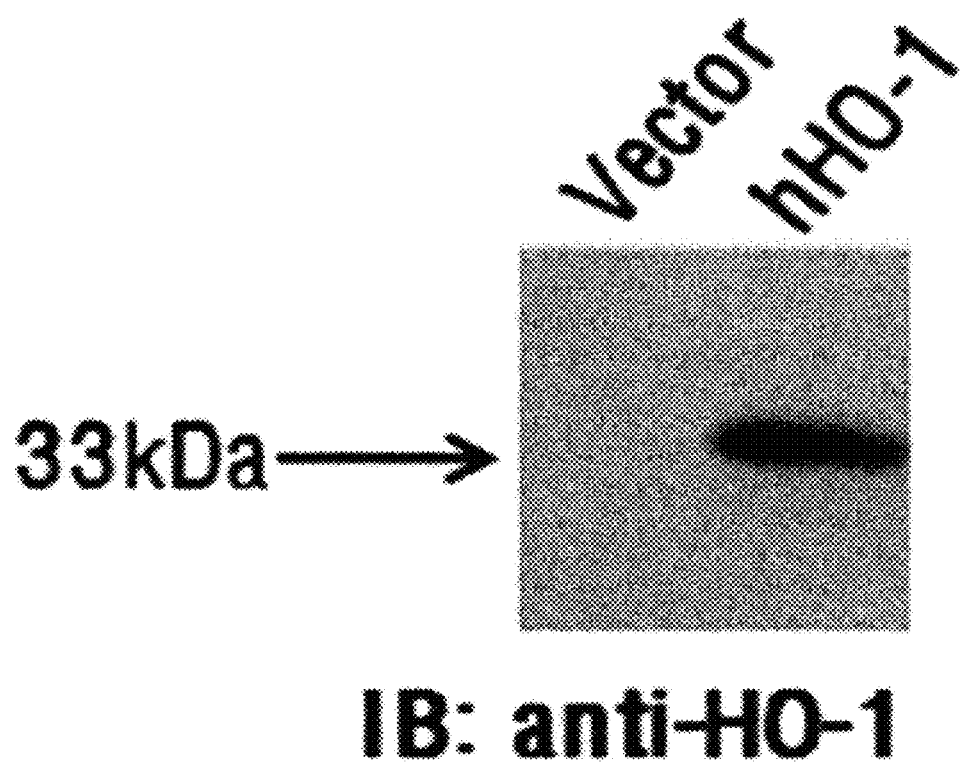
FIG. 3 shows the results of Western blotting to examine the expression of human HO-1 protein in the gene coding for human HO-1 protein-inserted expression vector.
Figure 4:
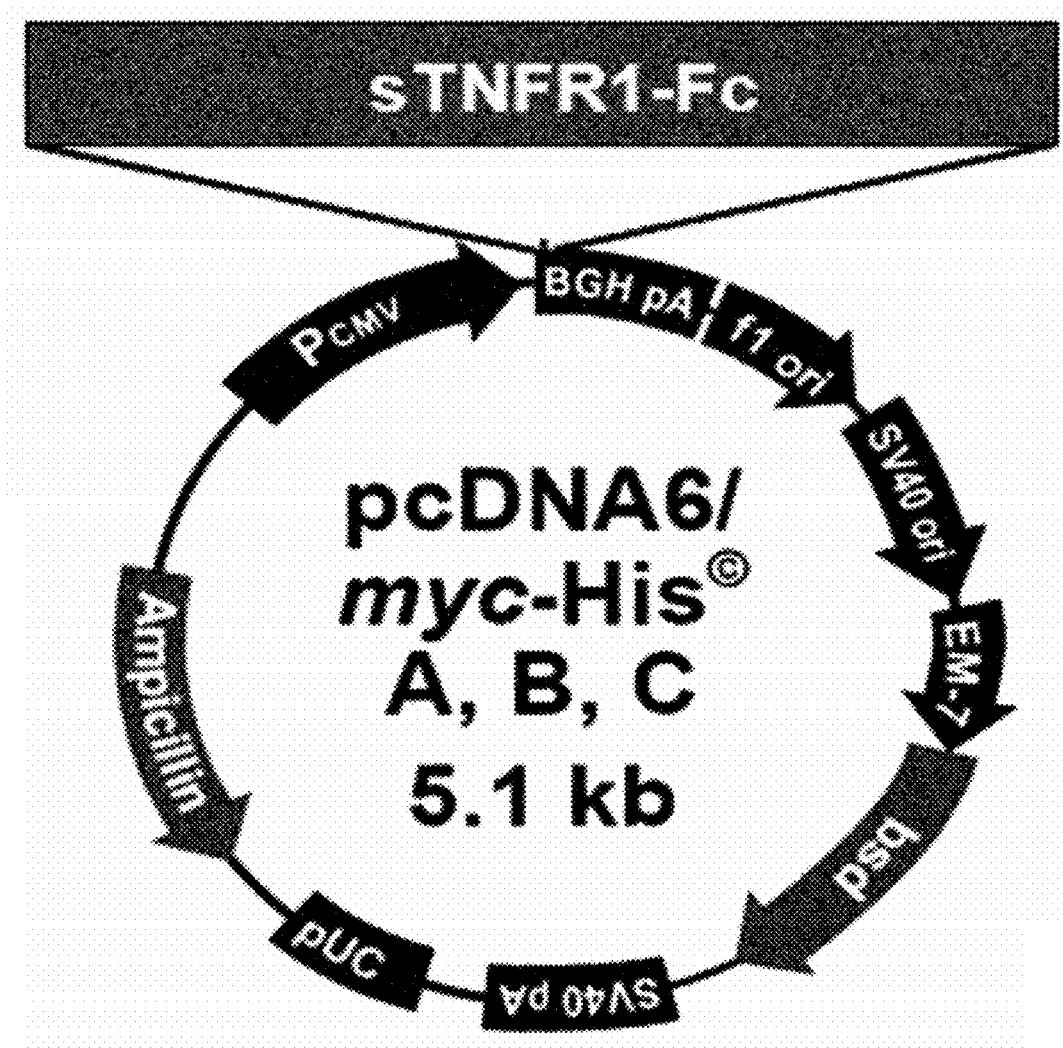
FIG. 4 is a schematic view of a cleavage map of a gene coding for human sTNFR1-Fc fusion protein-inserted expression vector.
Figure 6:
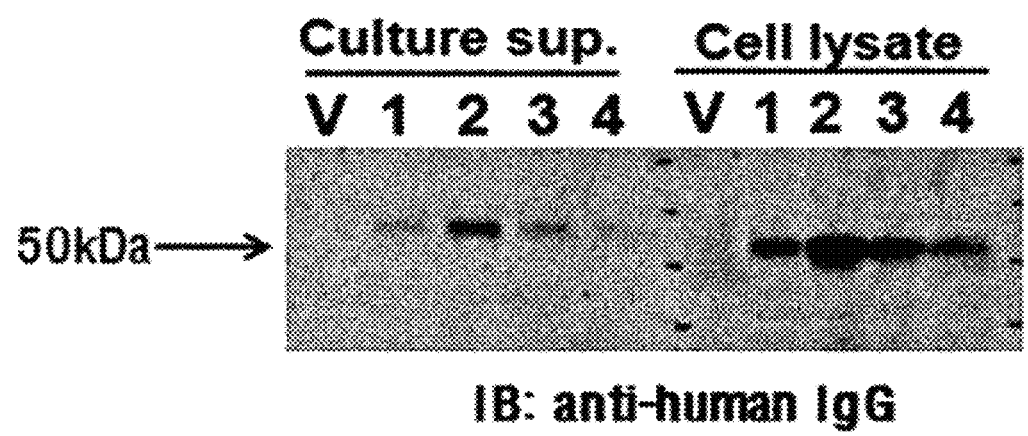
FIG. 6 shows the result of Western blotting to examine the expression of human sTNFR1-Fc fusion protein in the gene coding for human sTNFR1-Fc fusion protein-inserted expression vector.

In one preferred embodiment, step b) may be performed by introducing a single vector comprising the gene coding for human HO-1 protein, preferably, a vector having a cleavage map of FIG. 1, and a single vector comprising the gene coding for human TNFR1-Fc fusion protein, preferably, a vector having a cleavage map of FIG. 4 into somatic cells, sequentially or simultaneously. In one specific Example of the present invention, the gene coding for human HO-1 protein was inserted into the pcDNA3.1 vector which is an expression vector comprising the neomycin resistance gene, so as to prepare the vector having the cleavage map of FIG. 1, and expression of the inserted gene was examined in HEK239 cell line (FIG. 3). In addition, the gene coding for human TNFR1-Fc fusion protein was inserted into the pcDNA6 vector which is an expression vector comprising the blasticidin resistance gene, so as to prepare the vector having the cleavage map of FIG. 4, and expression of the inserted gene was examined in HEK239 cell line (FIG. 6).

As used herein, the term "vector" refers to an expression vector capable of expressing a target gene in cells introduced with the vector, and to a gene construct that includes essential regulatory elements to which a gene insert is operably linked in such a manner as to be expressed. Preferably, in the present invention, a recombinant vector comprising the gene coding for human HO-1 protein or the gene coding for human TNFR1-Fc fusion protein can be prepared, and the prepared recombinant vector is introduced into somatic cells, thereby preparing a donor cell line for the production of the transgenic embryos.

Preferably, the promoter used in the present invention may be any promoter commonly used in the art for the preparation of expression vectors, without limitation. Examples of the promoter to be used may include a CMV promoter, an SV40 promoter, and a CAG promoter, but the promoter sequences to be used in the present invention are not limited to these examples. If necessary, a particular promoter may be used for tissue-specific expression.

Preferably, the polyadenylation sequence of the present invention may be a commonly used polyadenylation sequence, for example, an SV40 polyadenylation sequence, a human growth hormone polyadenylation sequence, a mouse protamine-1 gene polyadenylation sequence (protamine-1 poly A signal), a large T antigen poly A region-derived polyadenylation sequence, rabbit β-globin-derived polyadenylation sequence or fetal bovine growth hormone polyadenylation sequence without limitation.

In order to examine expression of the gene coding for human HO-1 protien or the gene coding for human TNFR1-Fc fusion protein, the vector of the present invention may further include a tag sequence for isolation or purification of protein. Examples of the tag sequence may include GFP, GST (Glutathione S-transferase)-tag, HA, His-tag, Myc-tag, T7-tag, but the tag sequence of the present invention is not limited to these examples.

Figure 9:
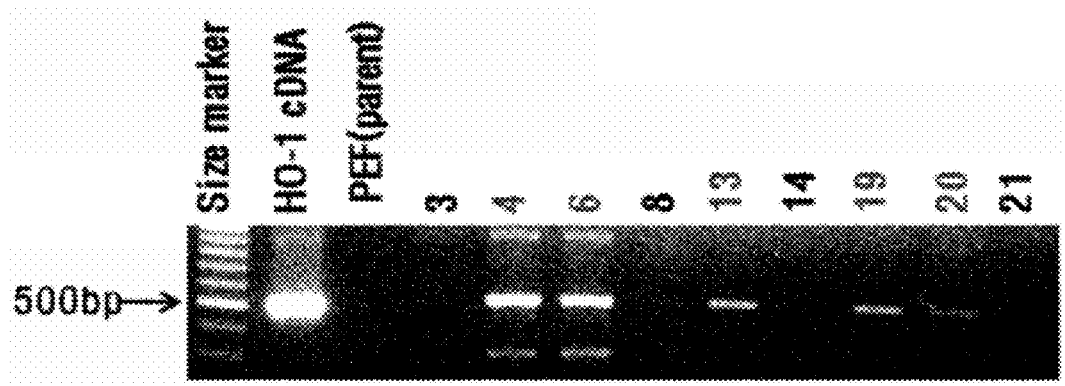
FIG. 9 shows the result of PCR to examine insertion of the gene coding for human HO-1 protein in a somatic donor cell line.
Figure 10:
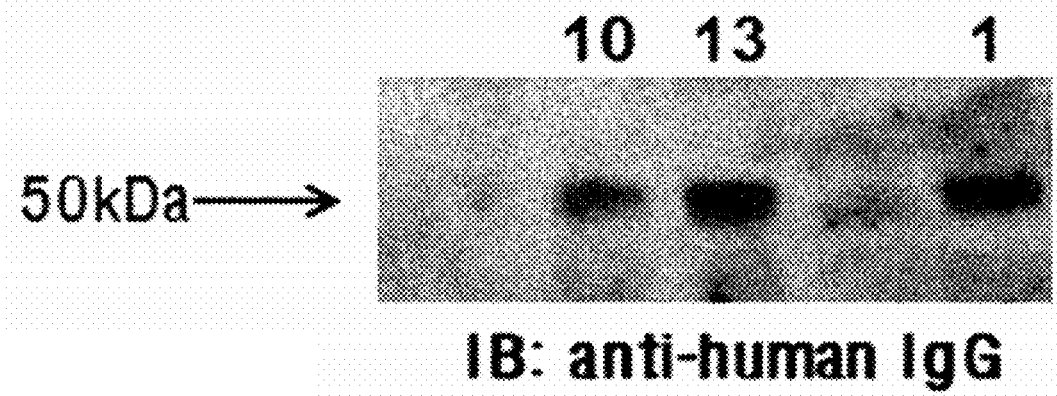
FIG. 10 shows the result of Western blot to examine the sTNFR1-Fc expression in the somatic donor cell line.

In one preferred embodiment, the somatic cells introduced with the expression vector of step b) can be easily selected by using the expression vector introduced with a selection marker, in step c). The selection marker may be an antibiotic resistance gene. Examples of the antibiotic resistance gene may include $bsd^r$, $neo^r$, $pac^r$, $bsr^r$, and $hph^r$, but are not limited thereto. In one specific Example of the present invention, the somatic cells introduced with the expression vector comprising the gene coding for human HO-1 protein were selected using $neo^r$ by treatment of the cell culture broth with neomycin (FIG. 9), and the somatic cells introduced with the expression vector including the gene coding for human TNFR1-Fc fusion protein were selected using $bsd^r$ by treatment of the cell culture broth with blasticidin (FIG. 10).

In one preferred embodiment, immature oocytes may be collected from the ovary of gilts, cultured, and used as the oocyte of the present invention, in step d).

As used herein, the term "nuclear transfer" means transfer of the nucleus of a cell into an enucleated oocyte, and an individual born by implantation of the nuclear transferred embryos is a genetically identical animal clone because genetic material of the same donor cell is transferred into the recipient cytoplast.

To remove the genetic materials of the oocytes, various methods such as physical enucleation, chemical treatment and centrifugation with Cytochalasin B treatment are employed (Tatham et al., *Hum Reprod.*, 11(7); 1499-1503, 1996). In the present invention, the physical enucleation method using a micromanipulator was used. A gene-targeted somatic cell is introduced into an enucleated oocyte by using the techniques such as cell fusion method, intracytoplasmic microinjection, or the like. The cell fusion method is simple and useful for large production of embryos. The intracytoplasmic microinjection permits maximum exposure of a nucleus to the cytosol in recipient cytoplasts. The fusion of somatic cell and enucleated oocyte is accomplished by changing viscosity on cell surface by electric pulse. It is convenient to use an electro-cell manipulator that the pulse length and voltage are easily controllable. In the specific Example of the present invention, physical enucleation was performed by micromanipulation, and fusion of the enucleated oocyte and the selected somatic donor cell line was performed by electric pulse to prepare embryos.

In one preferred embodiment, the surrogate mother for implantation of the somatic cell nuclear transferred embryo is preferably an individual in estrus, in step e).

The nuclear-transferred embryos are activated and developed to the implantable stage, and then implanted to the surrogate mother. The activation of cloned embryo induces reinitiation of cell cycle, which is temporarily quiescent, whereby the cleavage of embryo is possible. To activate a cloned embryo, the activation of cell cycle arrest factors, such as MPF, MAP kinase or the like, should be suppressed, in which for the suppression of the activation, the increase of intracellular calcium ion in a cloned embryo is necessary. The activation of cell cycle arrest factors can be directly suppressed by the dramatic increase of calcium influx induced by electro-stimulation or chemical treatment such as ionomycin, 6-DMAP or the like, in which the above methods can be used independently or together.

In the specific Example of the present invention, for evaluation of ex vivo functions of TNFR1-Fc fusion gene, it was found that porcine vascular endothelial cells increased expression of VCAM-1 by TNF-α stimulation (FIG. 7), and porcine vascular endothelial cell line transformed with the vector including the gene coding for TNFR1-Fc fusion protien of the present invention showed no changes in VCAM-1 expression by TNF-α stimulation (FIG. 8), indicating that TNF-α can be effectively suppressed by the gene coding for TNFR1-Fc fusion protein (Example 2). These results imply that the transgenic pig expressing the gene coding for TNFR1-Fc fusion protein of the present invention is able to reduce TNF-α-mediated inflammatory responses and also suppress immune rejection response in xenotransplantation.

Further, in the specific Example of the present invention, expressions of the gene coding for HO-1 protein and TNFR1-Fc fusion protein in the nuclear donor cell line were examined by RT-PCR (FIG. 9) and Western blotting (FIG. 10), respectively. These results imply that the islet cells of the transgenic pig of the present invention show a resistance to oxidative stress when isolated and can be protected through apoptosis prevention, and TNF-α-mediated inflammatory responses after transplantation can be reduced, and maturation of dendritic cells can be inhibited, and proliferation and activation of T cells can be controlled to reduce immune rejection response, thereby suppressing immune rejection responses and promoting early engraftment rate of islet xenotransplants at the same time.

Figure 11:
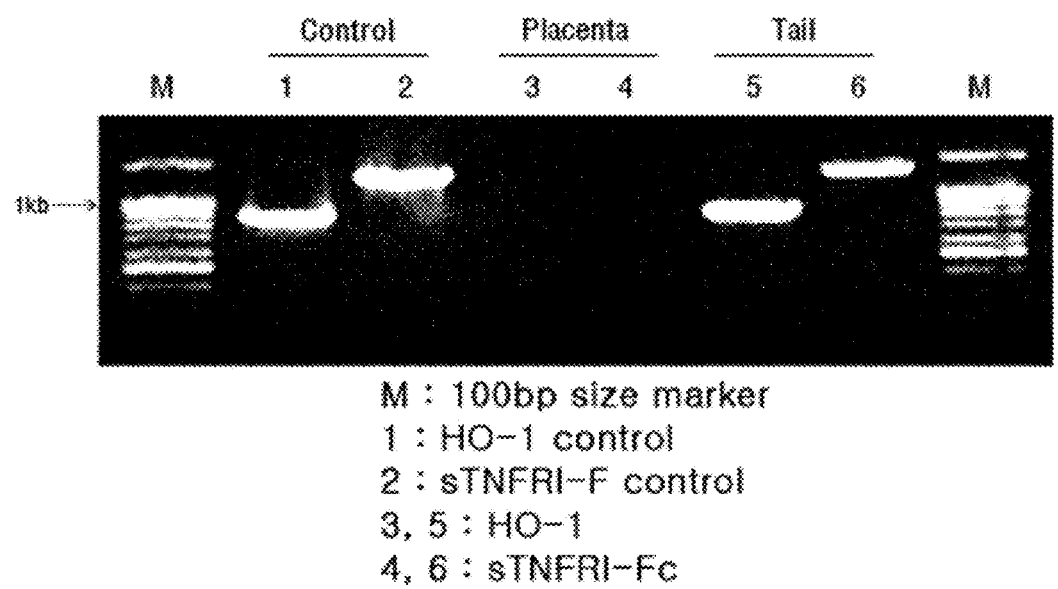
FIG. 11 shows the result of PCR to examine expression of the gene coding for HO-1 protein and sTNFR1-Fc protein in a transgenic pig.

In the specific Example of the present invention, stable expression of the gene coding for HO-1 protein and the gene coding for TNFR1-Fc fusion protein in the transgenic pig produced by the method of the present invention was examined by PCR (FIG. 11).

Moreover, in the specific Example of the present invention, newborn piglet islets were transfected with adenoviruses expressing GFP, sTNFR1-Fc, and HO-1 (Ad-GFP, Ad-sTNFR1-Fc, Ad-HO1), respectively and their survival rates under normoxic and hypoxic conditions were analyzed by MTT assay. As a result, each of the cell survival rates under hypoxic conditions was increased to approximately 40% and 60% in the group transfected with Ad-HO-1 and in the group co-transfected with Ad-sTNFR1-Fc and Ad-HO1, compared to the group transfected with no adenovirus (FIG. 12). These results indicate that the use of the pig expressing sTNFR1-Fc and HO-1 of the present invention increases the survival rate of cell or tissue transplants, suppresses rejection responses and protects organs from oxidative stress, compared to the known organ transplantation conditions where immune responses are commonly increased under hypoxic conditions, thereby increasing immune rejection responses and damage of islet transplant due to oxidative stress.

Accordingly, the results suggest that the method of producing the transgenic pig of the present invention is used to stably express the gene coding for human HO-1 protein and the gene coding for TNFR1-Fc fusion protein, thereby protecting cells or tissues from oxidative stress during islet transplantation for the treatment of diabetes and during organ transplantation, and also to produce a pig showing suppressed immune rejection responses during organ transplantation.

In another aspect, the present invention relates to a transgenic pig suppressed in immune rejection response for organ transplantation that is produced by the above method.

In one preferred embodiment, the organ may include any organ of pigs without limitation, as long as it can be transplanted into human, and preferably islets.

As used herein, the term "islet" means Langerhans islet, and islet transplantation is a viable treatment for the amelioration of type I diabetes. However, the processes of clinical islet transplantation are made difficult by a number of factors. One factor is primary nonfunction (PNF) of the graft. Another is the need for high numbers of donor islets needed for a successful reversal of diabetes. Both situations reflect the same pathophysiology: the substantial cell loss in the graft within the first week after transplantation. After transplantation, islets suffer a variety of stress factors such as hypoxia before secondary vascularization and exposure to pro-inflammatory cytokines and free radicals released from macrophages in the microenvironment of the transplant and from resident islet macrophages. The toxic effects of immunosuppressive drugs as well as rejection also contribute to islet cell loss. The existence of PNF after experimental syngeneic islet transplantation indicates that non-specific inflammation plays a major role in this scenario.

Therefore, the above problems can be addressed by using the organs extracted from the transgenic pig expressing the gene coding for human HO-1 proteine and the gene coding for human TNFR1-Fc fusion protien that is produced by the method of the present invention, thereby providing an innovative therapy for diabetes.

In still another aspect, the present invention relates to a somatic donor cell line for producing the transgenic pig.

In one preferred embodiment, any somatic donor cell line may be used without limitation, as long as it is able to stably express the gene coding for human HO-1 protein and the gene coding for human TNFR1-Fc fusion protein, and preferably a somatic donor cell line identified by accession number KCLRF-BP-00225.

According to the method of the present invention, the gene coding for human HO-1 protein and the gene coding for human TNFR1-Fc fusion ptorein were efficiently transfected into porcine somatic cells, and a porcine somatic donor cell line expressing the gene coding for human HO-1 protein and the gene coding for human TNFR1-Fc fusion protein was selected. The somatic donor cell line is characterized in that the expression vector is located at the same site in the genome. If the somatic donor cell line is not introduced with the expression vector, insertion sites of the gene differ between the somatic cells, even though the gene is introduced. Protein expression patterns may differ depending on gene insertion sites in the chromosome, and thus pigs produced using these cells showed different expression patterns of introduced genes between individuals. In the specific Example of the present invention, a somatic donor cell line was established in order to solve the problems, and deposited at the Korean Cell Line Bank (7$^{th}$ floor, Cancer Research Institute, school of medicine, Seoul National University, 28, Yeongeon-dong, Jongno-gu, Seoul) under the Accession No. KCLRF-BP-00225 on Dec. 28, 2009.

In still another aspect, the present invention relates to a method for producing the transplantable organs from the transgenic pig suppressed in immune rejection response, comprising the steps of producing the transgenic pig by the above method for producing the transgenic pig; and isolating the organ from the transgenic pig.

In one preferred embodiment, the organs may include any organ that can be transplanted into human without limitation, and preferably islets. In addition, when the organ is transplanted into human, immune rejection responses do not occur, thereby treating diseases associated with the type of the desired organ. Preferably, diabetes can be treated by islet transplantation.

Hereinafter, the present invention will be described in more detail with reference to Examples. However, these Examples are for illustrative purposes only, and the invention is not intended to be limited by these Examples.

EXAMPLE 1

Construction of the Gene Coding for HO-1 Protein and the Gene Coding for sTNFR1-Fc Protein-Expressing Vectors and Test on Their Expressions 1-1. Construction of the Gene Coding for HO-1 Protein-Expressing Vector and Test on Gene Expression The sequence of the gene coding for human Heme oxygenase-1 (HO-1) protein was analyzed using NCBI web site (http://www.ncbi.nlm.nih.gov/) and ExPASy web site (http://expasy.org/), and was used to prepare its forward (SEQ ID NO: 2) and reverse primers (SEQ ID NO: 3). Polymerase Chain Reaction (PCR) was performed using the primer set to obtain the gene coding for HO-1 protien (SEQ ID NO: 1 and FIG. 2). For expression of the gene, a pcDNA3.1 vector (Invitrogen, CA, USA), which is an expression vector comprising a neomycin resistance gene, was treated with NheI and EcoRI restriction enzymes, and the obtained the gene coding for HO-1 protein was inserted into the restriction sites so as to construct a gene coding for HO-1 protein-expressing vector.

In order to examine expression of the inserted gene, HEK293 cell line was transfected with the gene coing for HO-1 protein-expressing vector using Lipofectamine™2000 (Invitrogen, CA, USA). The HEK293 cell line was seeded in a 35 mm plastic culture dish (Becton Dickinson, NJ, USA) at a cell density of $3\times10^5$, and at the next morning, 1 μg of HO-1-expressing vector was diluted with 50 μl of Opti-MEM I Reduced Serum Medium (Invitrogen, CA, USA), and Lipofectamine™2000 in the equal volume to the HO-1-expressing vector was also diluted with 50 μl of Opti-MEM I, and incubated at room temperature for 5 minutes. After incubation, the diluted HO-1-expressing vector and the diluted Lipofectamine™2000 were mixed with each other, and incubated at room temperature for 20 minutes. After incubation, the mixture was added to the cells in the 35 mm cell culture dish, and cultured at 37° C. in $CO_2$ incubator. After 4 hours, the media was replaced with DMEM (Invitrogen, CA, USA) supplemented with 10% FBS and penicillin/streptomycin, and cultured at 37° C. in $CO_2$ incubator. After 48 hours, cells were harvested using a lysis buffer (lysis buffer: 1% Triton X-100, 50 mM TrisHCl, 20 mM NaF, 150 mM NaCl, protease inhibitors), and 30 μg of cell lysate was electrophoresed and then transferred onto a PVDF membrane. The PVDF membrane was blocked with a blocking buffer (5% skim milk in TBST) for 1 hour, and reacted with anti HO-1 antibody (rabbit monoclonal antibody, Abcam, Cambridge, UK) diluted at 1:2000 at room temperature for 1 hour. After reaction, the membrane was washed with TBST buffer for 30 minutes three times, and reacted with HRP-conjugated anti-rabbit IgG antibody (Santa Cruz Biotechnology, CA, USA) diluted at 1:5000 at room temperature for 1 hour. After reaction, the membrane was washed with TBST buffer for 30 minutes three times, and treated with chemiluminescent substrates (WestSaveUp™, Abfrontier, Seoul, Korea), followed by exposure to X-ray film and development (FIG. 3).

As a result, expression of 33 kDa of the gene coding for human HO-1 protein inserted in the vector was observed (FIG. 3).

Figure 5:
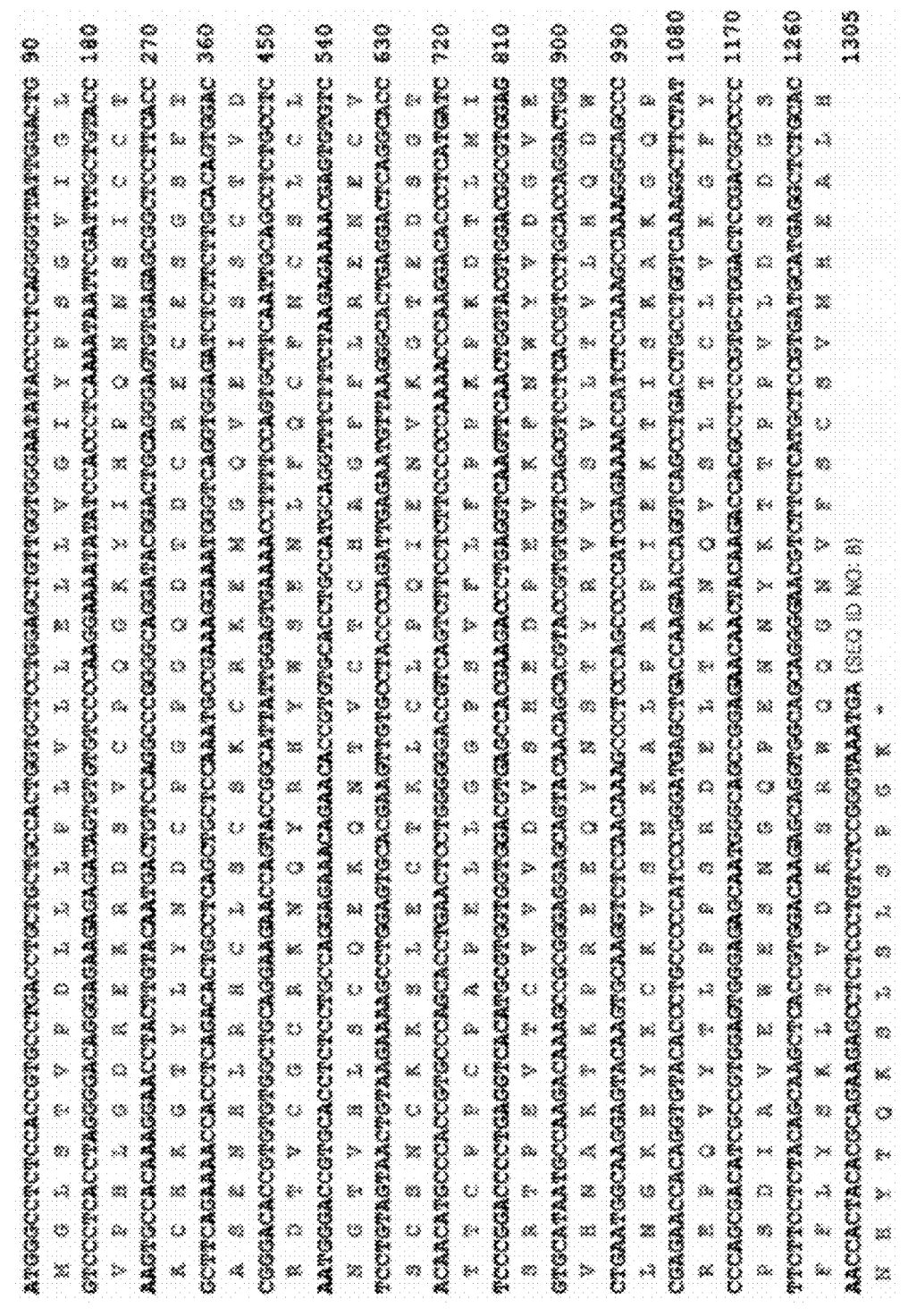

1.2. Construction of the Gene Coding for sTNFR1-Fc Fusion Protein-Expressing Vector and Test on Gene Expression The sequence of the gene coding for human tumor necrosis factor receptor 1 (TNFR1) protein was analyzed using NCBI web site (http://www.ncbi.nlm.nih.gov/) and ExPASy web site (http://expasy.org/), and was used to prepare forward (SEQ ID NO: 4) and reverse primers (SEQ ID NO: 5) of sTNFR1 of the extracellular domain of tumor necrosis factor receptor 1. In addition, the sequence of human immunoglobulin G1 gene was analyzed to prepare forward (SEQ ID NO: 6) and reverse primers (SEQ ID NO: 7) of Fc region. Polymerase Chain Reaction (PCR) was performed using each primer set to obtain soluble tumor necrosis factor receptor 1 (soluble TNFR1) and immunoglobulin G1-Fc (IgG1-Fc) fusion gene (sTNFR1-Fc, SEQ ID NO: 8 and FIG. 5). For expression of the gene, a pcDNA6 vector (Invitrogen, CA, USA), which is an expression vector including a blasticidin resistance gene, was treated with HindIII and XhoI restriction enzymes, and the obtained the gene coding for sTNFR1 and IgG1-Fc fusion protein was inserted into the restriction sites so as to construct a gene coding for sTNFR1-Fc protein-expressing vector.

In order to examine expression of the inserted gene, HEK293 cell line was transfected with the gene coding for sTNFR1-Fc protien-expressing vector using Lipofectamine™2000 (Invitrogen, CA, USA). The HEK293 cell line was seeded in a 35 mm plastic culture dish (Becton Dickinson, NJ, USA) at a cell density of $3\times10^5$, and at the next morning, 1 μg of the gene coding for sTNFR1-Fc protein-expressing vector was diluted with 50 μl of Opti-MEM I Reduced Serum Medium (Invitrogen, CA, USA), and Lipofectamine™2000 in the equal volume to the sTNFR1-Fc-expressing vector was also diluted with 50 μl of Opti-MEM I, and incubated at room temperature for 5 minutes. After incubation, the diluted sTNFR1-Fc-expressing vector and the diluted Lipofectamine™2000 were mixed with each other, and incubated at room temperature for 20 minutes. After incubation, the mixture was added to the cells in the 35 mm cell culture dish, and cultured at 37° C. in $CO_2$ incubator. After 4 hours, the media was replaced with serum-free DMEM (Invitrogen, CA, USA) supplemented with penicillin/streptomycin, and cultured at 37° C. in $CO_2$ incubator. After 48 hours, the culture broth and cell lysate were subjected to Western blotting using anti-hIgG antibody (Santa Cruz Biotechnology, CA, USA). The cell lysate and culture broth was electrophoresed, and then transferred onto a PVDF membrane. The PVDF membrane was blocked with a blocking buffer (5% skim milk in TBST) for 1 hour, and then reacted with HRP-conjugated anti-human IgG antibody (Santa Cruz Biotechnology, CA, USA) diluted at 1:5000 at room temperature for 1 hour. After reaction, the membrane was washed with TBST buffer three times, and treated with chemiluminescent substrates (WestSaveUp™, Abfrontier, Seoul, Korea), followed by exposure to X-ray film and development (FIG. 6).

As a result, 50 kDa of bands binding to IgG were observed in the culture broth and cell lysate, indicating protein expression of soluble TNFR1-Fc (FIG. 6).

EXAMPLE 2

Evaluation of Ex Vivo Functions of the Gene Coding for sTNFR1-Fc Fusion Protein

In order to examine the inhibitory effects of the expressed the gene coding for sTNFR1-Fc fusion protein on TNF-α, expression of VCAM-1 protein that is known to increase by TNF-α stimulation was examined. An aortic endothelial cell line (MPN3 cell) was stimulated with 20 ng/ml of TNF-α. After 12 and 24 hours, flow cytometry was performed using VCAM-1 antibody.

For flow cytometry, trypsin-treated cells were washed with PBS (Phosphate Buffered Saline) three times, and treated with 10 μg/ml of anti-VCAM-1 antibody (rabbit polyclonal) and reacted on ice for 30 minutes. After reaction, the cells were washed with PBS three times, and treated with secondary antibody FITC (fluorescein isothiocyanate)-conjugated rabbit IgG antibody at 1:500, and reacted on ice for 30 minutes in the dark. After reaction, the cells were washed with PBS three times, and analyzed on a FACSCalibur (Becton-Dickinson, CA, USA) using CELLQUEST software.

Figure 7:
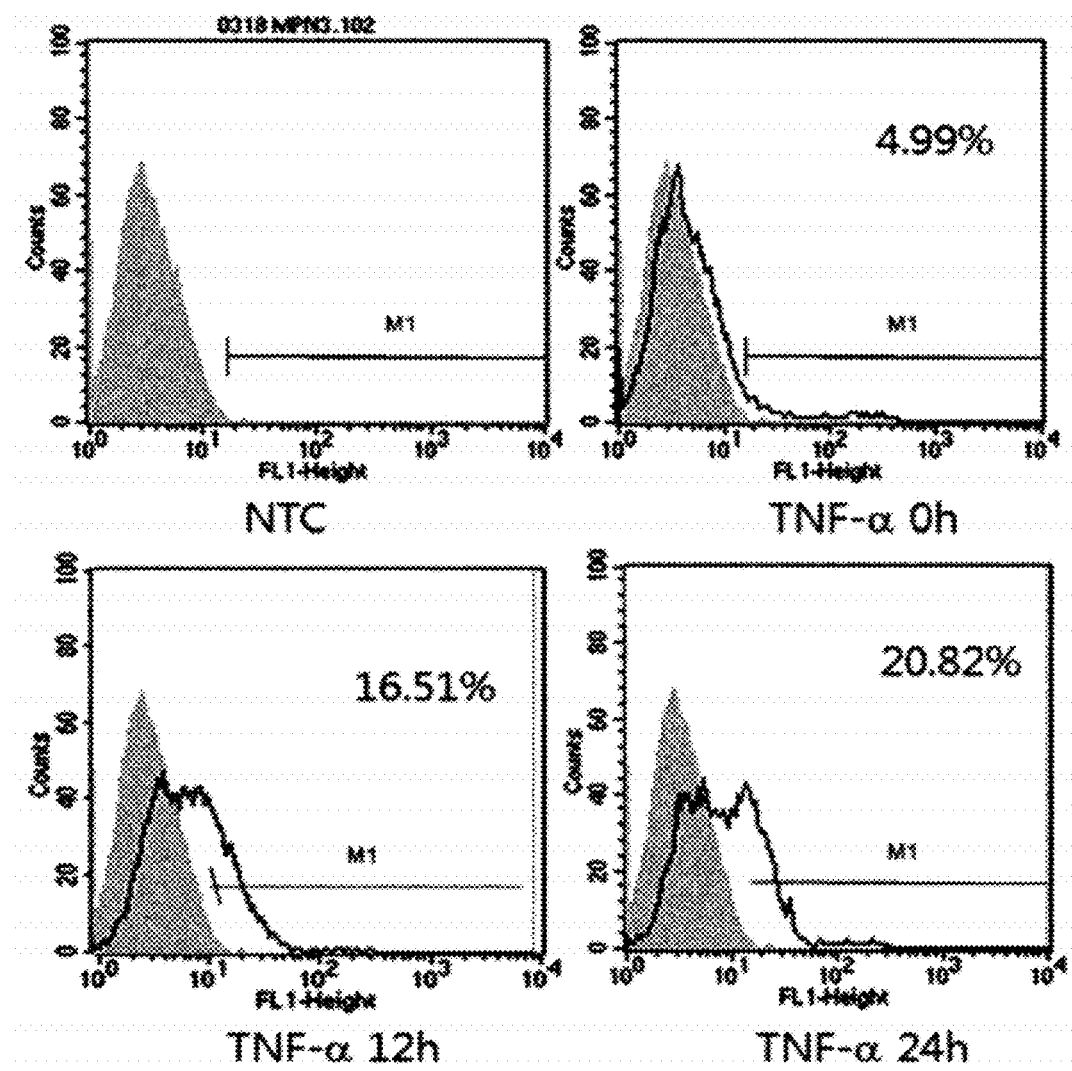
FIG. 7 shows the result of flow cytometry to examine an increase in VCAM-1 molecule expression in porcine vascular endothelial cells after treatment of TNF-α.

As a result, VCAM-1 expression in the porcine aortic endothelial cell line was found to be increased by TNF-α stimulation according to stimulation time (FIG. 7).

sTNFR1-Fc and the empty vector (pcDNA3.1-Hygro(+)) were introduced into the porcine aortic endothelial cell line by electroporation. After 48 hour incubation, TNF-α treatment was performed. After 24 hours of TNF-α treatment, flow cytometry was performed using VCAM-1 antibody.

Figure 8:
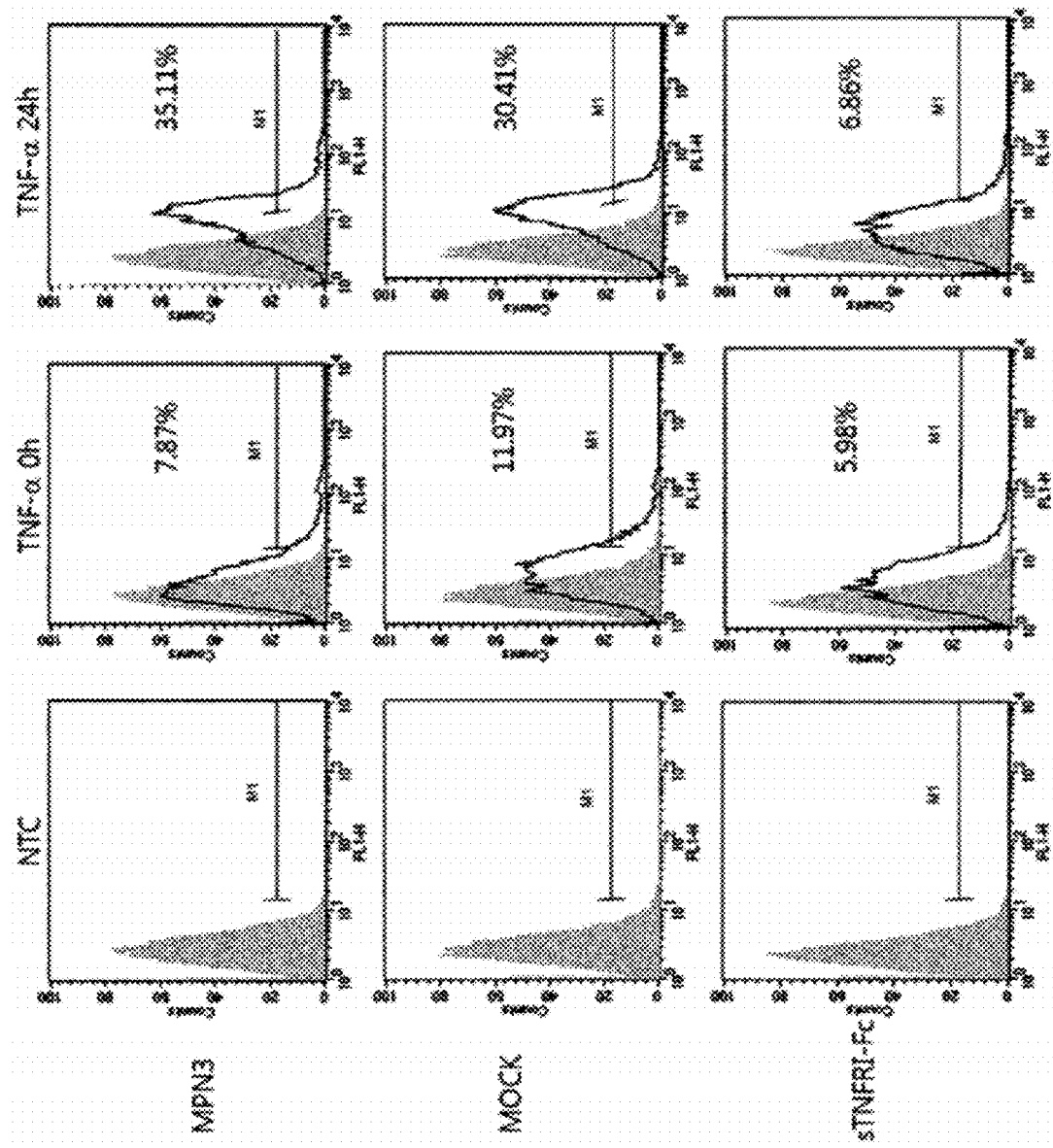
FIG. 8 shows the result of flow cytometry to examine inhibitory effects on VCAM-1 molecule expression in gene coding for human sTNFR1-Fc fusion protein-expressed cells after treatment of TNF-α.

24 hours after TNF-α stimultation, increased VCAM-1 expression was observed in the groups introduced with no gene and introduced with the empty vector. On the contrary, no difference in VCAM-1 expression was observed in the group introduced with the gene coding for sTNFR1-Fc protein even at 24 hours after TNF-α stimultation. These results indicate that the sTNFR1-Fc-expressing cells are able to effectively inhibit TNF-α stimulation (FIG. 8).

EXAMPLE 3

Isolation and Culture of Nuclear Donor Cell

Fibroblasts obtained from fetal pigs were used as a nuclear donor cell. Firstly, fetal pigs were obtained from mother pigs between day 25 to 35 of gestation by cesarean (section). The skin on the back of the fetal pig was isolated using a scalpel blade, and washed with DPBS (Dulbecco's Phosphate Buffered Saline) three times, and minced. The minced skin tissues were put in DMEM (Dulbecco's modified Eagle's medium) medium (Gibco Life Technologies, MD, USA) containing 0.25% trypsin and 1 mM EDTA at 37° C. for 1 hour. The trypsin-treated cells were washed with $Ca^{2+}$ and $Mg^{2+}$-free DPBS once, and centrifuged at 300×g for 2 minutes, and then inoculated in a 60 mm plastic culture dish (Becton Dickinson, NJ, USA). Next, the cells were cultured in DMEM containing 10% (v/v) FBS, 1 mM glutamine, 25 mM $NaHCO_3$ and 1% (v/v) minimum essential medium (MEM) non-essential amino acid solution (Invitrogen, CA, USA) at 39° C. and in 5% $CO_2$ and 95% air for 3-4 days. The cells were cultured until saturation, and then cells not attached to the culture dish were removed, and the attached cells were detached from the culture dish by treatment in the medium containing 0.1% trypsin and 0.02% EDTA for 1 minute, and transferred to three new culture dishes for subculture at 4-6 day intervals.

For cryopreservation, cells were detached from the culture dish by treatment with a medium containing 0.1% trypsin and 0.02% EDTA for 1 minute, and then put in a freezing medium composed of 80% (v/v) DMEM, 10% (v/v) DMSO, and 10% (v/v) FBS, and aliquoted into cryotubes, followed by storage at −196° C. in liquid nitrogen.

EXAMPLE 4

Preparation of Somatic Donor Cell Line

Porcine fibroblasts were seeded in a 35 mm plastic culture dish (Becton Dickinson, NJ, USA) at a density of $3\times10^5$ cells/well, and in the next morning, each 1 µg of gene-expressing vectors constructed in Example 1 (pcDNA3.1/HO1, pcDNA6/sTNFR1-Fc) and linearized by the restriction enzyme ScaI was diluted with 50 µl of Opti-MEM I Reduced Serum Medium (Invitrogen, CA, USA), and Lipofectamine™2000 in the equal volume to each gene expressing vector was also diluted with 50 µl of Opti-MEM I, and incubated at room temperature for 5 minutes. After incubation, the diluted sTNFR1-Fc-expressing vector and the diluted Lipofectamine™2000 were mixed with each other, and incubated at room temperature for 20 minutes. After incubation, the mixture was added to the cells in the 35 mm cell culture dish, and cultured at 37° C. in $CO_2$ incubator. After 4 hours, the media was replaced with DMEM (Invitrogen, CA, USA) supplemented with 10% FBS and penicillin/streptomycin, and cultured at 37° C. in $CO_2$ incubator. After 2 days, cells were treated with trypsin (Sigma, MO, USA), and transferred to a 100 mm culture dish (Becton Dickinson, NJ, USA). After 2 days, the medium was replaced with DMEM (10% FBS, penicillin/streptomycin) containing 1500 µg/ml of G418(Invitrogen, CA, USA) and cultured in a 37° C. $CO_2$ incubator. The cells were cultured for 1-2 weeks, while the medium was replaced every 2 days to remove dead cells. Next, the cells were cultured for 1 week, while the medium was replaced with a medium (DMEM, 10% FBS, penicillin/streptomycin) containing 100 µg/ml of G418 and 5 µg/ml of blasticidin (Sigma, MO, USA) every 2 days. Thereafter, the cells were cultured in a medium containing 100 µg/ml of G418 and 1 µg/ml of blasticidin. When colonies were observed to grow, 50 or more colonies were selected using yellow tips, and transferred to a 48-well plate (Becton Dickinson, NJ, USA). According to cell growth, each colony was transferred to a 12-well plate, a 6-well plate, and a 60 mm culture dish. When the cells were transferred to the 6-well plate, a small amount of cells were taken and eluted to isolate DNA. Then, PCR was performed using HO-1-specific primers, HO-1 forward (SEQ ID NO: 2) and reverse primers (SEQ ID NO: 9), the genomic DNA isolated from the cells as a template, and Taq polymerase (Cosmogentech, Seoul, Korea) under the conditions consisting of denaturation at 95° C. for 5 minutes, 30 cycles of at 95° C. for 30 seconds, at 58° C. for 30 seconds, and at 72° C. for 30 seconds, and elongation at 72° C. for 10 minutes, so as to examine HO-1 insertion (FIG. 9).

After SDS-PAGE, Western blotting was performed using anti-human IgG antibody (Santa Cruz Biotechnology, CA, USA) to examine expression of sTNFR1-Fc protein (FIG. 10).

For Western blotting, cell lysate was subjected to electrophoresis, and then transferred to a PVDF membrane. Thereafter, the PVDF membrane was blocked with a blocking buffer (5% skim milk in TBST) for 1 hour. After blocking, the membrane was reacted with HRP-conjugated anti-human IgG antibody (Santa Cruz Biotechnology, CA, USA) diluted at 1:5000 at room temperature for 1 hour. After reaction, the membrane was washed with TBST buffer three times, and reacted with chemiluminescent substrates (WestSaveUp™, Abfrontier, Seoul, Korea), followed by exposure to the X-ray film and development (FIG. 10).

After examination of the expression, the cells were transferred to a 100 mm culture dish and proliferated, and aliquoted to 10 cryovials, followed by cryopreservation. The established cell line was designated as HO-1/sTNFRI-Fc line 1, and then deposited at the Korean Cell Line Bank under the Accession No. KCLRF-BP-00225 on Dec. 28, 2009.

EXAMPLE 5

Collection of Immature Porcine Oocyte and Ex Vivo Maturation

Ovaries were collected from gilts at a slaughterhouse and transported to the laboratory in 0.9% saline solution at 30-35° C. Immature oocytes with follicular fluid and cumulus cells were aspirated and collected from 2-6 mm follicles using an 18 gauge needle attached to a 10 ml syringe. The aspirated follicular fluid was held at 37° C. in water bath, and precipitates were only placed in TLHEPES-PVA containing 0.1% PVA (polyvinyl alcohol) (114 mM NaCl, 3.2 mM KCl, 2 mM $NaHCO_2$, 0.4 mM $NaH_2PO_4$, 0.27 mM glucose, 10 mM sodium lactate, 2 mM $CaCl_2 2H_2O$, 0.5 mM $MgCl_2 6H_2O$, 10 mM HEPES, 0.03 mM phenol red, 0.25 mM sodium pyruvate, 0.3% BSA (bovine serum albumin), 75 µg/ml penicillin G and 25 µg/ml gentamycin sulfate) to collect immature oocytes only. Immature oocytes having tightly attached cumulus cells were only selected, and washed with TL-HEPES-PVA twice, and then washed with the following maturation medium twice. For Ex vivo maturation, TCM (tissue culture medium) 199 culture medium (Sigma, St. Louis, Mo., USA) was used as a basic medium, and supplemented with 26.19 mM $NaHCO_2$, 0.2 mM sodium pyruvate, 75 µg/ml sodium penicillin G, and 50 µg/ml streptomycin sulfate. An ex vivo medium containing 5 µg/ml insulin, 0.5 µg/ml LH (luteinizing hormone), 0.5 µg/ml FSH (follicular stimulating hormone), 10 ng/ml EGF (epidermal growth factor), 0.57 mM cysteine and 10% porcine follicular fluids (pFF) was prepared in a 4-well plate (NUNC), and immature oocytes were transferred thereto, followed by cultivation at 38.5° C. in a 5% $CO_2$ incubator for 22 hours. Thereafter, the immature oocytes were cultured in a maturation medium excluding FSH and LH for further 22 hours. The follicular fluids were those that had been collected from the ovaries obtained at a slaughterhouse, filtered, and frozen.

EXAMPLE 6

Somatic Cell Cloning

Oocytes matured for 1 to 44 hours were transferred to TL-HEPES-PVA supplemented with 0.1% hyaluronidase, and expanded cumulus cells were removed by pipetting. Enucleation of porcine oocytes was performed by micromanipulation under an inverted microscope (Nikon, Japan) equipped with a micromanipulator (Narishige, Japan), and porcine fibroblasts which is a donor cell transformed with the gene coding the HO-1 and sTNFR1-Fc fusion protein prepared in Example 4 were injected into the oocytes. For fusion of the different cells, an ECM 2001 electrocell manipulator (BTX Inc., San Diego, Calif., USA) was used to apply an electric stimulation of 1.5 kV/cm and 1 DC pulse for 60 µs. Fused oocytes were cultured in a TCM-199 medium for 3 hours, and then transferred to a PZM-3 medium, cultured, and used for transplantation of embryos.

EXAMPLE 7

Aspiration of Embryos

Aspiration of embryos was performed in a laboratory at which temperature is maintained (25-35° C.). A petri dish is filled with a medium for embryo transplantation, and embryos to be transplanted, which were prepared in Example 6, were added thereto. A 0.25 ml sterile straw for cell cryo-preservation was used. If possible, a commercial gamma irradiated straw is recommended. If necessary, it is also possible to directly sterilize it with EO gas (Ethylene Oxide).

Aspiration of embryos was performed in this order of media layer-air layer-media layer-air layer-embryo layer-air layer-media layer-air layer-media layer. During this procedure, special attention should be paid to sterilization of the straw. When the straw sterilized with EO gas is used, its interior was washed by repeating aspiration and dispensing of the medium for embryo transplantation 1-3 times, before aspiration of embryos. After completion of aspiration, the top end of straw was sealed by a plastic cap. To keep the aspirated and sealed straw sterile, a plastic pipette (Falcon, 2 ml) was cut in a slightly larger size than the straw, and put therein, and sealed with a paraffin film. The temperature of the sealed straw was maintained using a portable incubator, until shortly before use.

EXAMPLE 8

Production of Transgenic Pig by Transplantation of Embryos

Embryos and estrus-synchronized surrogate mothers were prepared. Transplantation of embryos was performed by exposure of ovary through laparotomy. After anesthetization of surrogate mothers, the mid-line of the abdominal region was incised to expose the uterus, ovary, oviduct, and fimbriae. The inlet of oviduct on the side of uterus was found inside the fimbriae. The straw aspirating embryos was aseptically taken from the portable incubator, and inserted into the inlet of oviduct. The inserted straw was then moved up to the ampullary-isthmic junction region. During this procedure, to minimize the temperature change of the straw, while its temperature was kept warm with the body temperature of the operator and the exposed uterus, the operation was rapidly performed. After the completion of insertion procedure, the straw was cut at the air containing layer on the opposite using scissors. A 1 cc syringe was mounted on the cut end, and approximately 0.3 cc air was injected to release the embryos and medium from the straw into the oviduct. At this time, 5 mm of the top end of a 0.2 ml yellow tip was cut off and used to connect the syringe and straw.

After completion of transplantation of embryos, the exposed uterus, ovary, oviduct, and fimbriae were put in abdominal cavity, and the abdominal fascia was closed using an absorbable suture material. Then, the surgical site was cleaned with Betadine, and treated with antibiotics and anti-inflammatory and analgesic drugs. A pregnancy test of the surrogate mother transplanted with embryos was performed, followed by induction of delivery of animals that successfully got pregnant. Finally, a transgenic pig introduced with HO-1 and sTNFR1-Fc was produced.

EXAMPLE 9

Test on Expression of the Gene Coding for HO-1 Protein and sTNFR1-Fc Proteinin Transgenic Pig In order to examine expression of the gene coding for HO-1 protein and the gene coding for sTNFR1-Fc ptorein in transgenic pigs, the placenta of surrogate mother and the umbilical cord of born transgenic pig were prepared in Example 8 during delivery of the transgenic pig.

Genomic DNAs were isolated from the placenta and umbilical cord tissues using a genomic DNA extraction kit (G-spin™ Genomic DNA Extraction Kit, iNtRON Biotechnology, Korea). Polymerase Chain Reaction was performed using the isolated genomic DNAs as a template, the gene coding for HO-1 protein-specific primers (SEQ ID NOs: 2 and 3) and sTNFR1-Fc protein-specific primers (SEQ ID NOs: 4 and 7), and a MaximeTM PCR premix kit so as to examine the presence of genes on the genomic DNAs (FIG. 11). Polymerase Chain Reaction was performed under the conditions consisting of denaturation at 95° C. for 5 minutes, 30 cycles of at 95° C. for 30 seconds, at 58° C. for 30 seconds, and at 72° C. for 1 minute, and elongation at 72° C. for 10 minutes.

As shown in FIG. 11, expression of the gene coding for HO-1 and sTNFR1-Fc protein was not observed in the placenta tissues of negative control, but expression of the gene coding for HO-1 and sTNFR1-Fc protein was observed in the umbilical cord tissue in the born transgenic pig, indicating production of desired transgenic pig.

EXAMPLE 10

Evaluation of Islet Function of the Gene Coding for sTNFR1-Fc Proteinand HO-1 Proein-Introduced Newborn Pig In order to evaluate functions of the gene coding for sTNFR1-Fc and HO-1 protein, the islets were isolated from 1-5 day-old newborn pigs, and used for the experiment. The isolated islets of the newborn pigs were cultured at 37° C. in $CO_2$ incubator for approximately 7 days, and then were transfected by treatment of the culture media with GFP, sTNFR1-Fc, and HO-1-expressing adenoviruses (Ad-GFP, Ad-sTNFR1-Fc, Ad-HO1), respectively. After treatment of the culture media with adenoviruses, the cells were cultured at 37° C. in $CO_2$ incubator for 24 hours, and then divided into normoxia and hypoxia groups. The normoxia group was cultured under general culture conditions, and the hypoxia group was cultured under hypoxic conditions of 37° C. and 1% $O_2$. After 24 hour-cultivation, in order to perform MTT assay, 20 newborn pig islets were hand-picked from each group, and put in a 96-well plate. Then, 10 µl of CCK-8 solution included in an MTT assay kit (Cell Counting Kit-8; CCK-8, Dojindo, Md., USA) was added thereto, and the cells were cultured at 37° C. in $CO_2$ incubator for 4 hours, and then O.D values at 450 nm were measured using a microplate reader.

As a result, a great difference in cell survival rate was not observed in the normoxia groups. However, under hypoxic conditions, approximately 40% and 60% increases in cell survival rate were observed in the Ad-HO-1-transfected group and the Ad-HO-1+Ad-sTNFR1-Fc-cotransfected group, respectively, compared to no adenovirus-transfected group (FIG. 12). In FIG. 12, Non represents a control group, Ad-GFP represents a group that is transfected with a GFP-expressing adenovirus, Ad-sTNFR1-Fc represents a group that is transfected with a sTNFR1-Fc-expresing adenovirus, Ad-HO-1 represents a group that is transfected with an HO-1-expressing adenovirus, and Ad-sTNFR1-Fc+Ad-HO-1 represents a group that is co-transfected with sTNFR1-Fc-expressing and HO-1-expresing adenoviruses. These results indicate that under hypoxic conditions during transplantation, the cells of the pig co-expressing sTNFR1-Fc and HO-1 of the present invention shows higher survival rate than those of the known pig, thereby suppressing rejection responses and protecting organs from oxidative stress during transplantation.

EFFECT OF THE INVENTION

Damage of islet cells by oxidative stress and early inflammatory responses during transplantation of islet cells greatly affect early engraftment rate of transplanted islet cells. Therefore, one of the methods for promoting early engraftment rate of the islet cells requires production of the islet cells showing resistance to oxidative stress and early inflammatory responses. When the transgenic pig co-expressing the gene coding for human HO-1 protein and TNFR1-Fc fusion protien of the present invention is used, oxidative stress can be reduced by the antioxidant actions and cell protective function of the gene coding for HO-1 protein during isolation and ex vivo culture of islets, and TNF-α-mediated inflammatory responses can be reduced by TNFR1-Fc expression at early transplantation, leading to promotion of early engraftment rate of islet cells. In addition, maturation of dendritic cells can be inhibited, and proliferation and activation of T cells can be controlled to reduce immune rejection response, thereby increasing survival rate of islet cells. Consequently, transplantation of the islet cells is useful for the treatment of diabetes.

What is claimed is:

1. A method for producing a transgenic pig, comprising:
   a) isolating somatic cells from a pig;
   b) introducing a gene coding for human HO-1 (Heme oxygenase-1) protein and a gene coding for human TNFR1-Fc (Tumor necrosis factor receptor 1-Fc) fusion protein into the somatic cells;
   c) selecting the somatic cells that are introduced with the genes;
   d) removing the nucleus from an oocyte of the pig and fusing it with the selected somatic cell to prepare a somatic cell nuclear transferred embryo; and
   e) implanting the embryo,
   wherein an organ of the transgenic pig is suppressed in immune rejection response during organ xenotransplantation.

2. The method according to claim 1, wherein the gene coding for human HO-1 protein of step b) has a nucleotide sequence of SEQ ID NO: 1.

3. The method according to claim 1, wherein the gene coding for human TNFR1-Fc fusion protein of step b) has a nucleotide sequence of SEQ ID NO: 8.

4. The method according to claim 1, wherein a single vector comprising the gene coding for human HO-1 protein and a single vector comprising the gene coding for human TNFR1-Fc fusion protein are introduced sequentially or simultaneously in step b).

5. The method according to claim 4, wherein the single vector comprising the gene coding for human HO-1 protein is a vector having a cleavage map of FIG. 1 and the single vector comprising the gene coding for human TNFR1-Fc fusion protein is a vector having a cleavage map of FIG. 4.

6. The method according to claim 1, wherein the selected somatic cell in step c) has Accession No. KCLRF-BP-00225.

7. A transgenic pig for organ xenotransplantation, which is produced by the method of claim 1, wherein an organ of the transgenic pig is suppressed in immune rejection response during organ xenotransplantation.

8. The transgenic pig according to claim 7, wherein the organ is an islet.

9. A transgenic pig for organ xenotransplantation, which is produced by the method of claim 6, wherein an organ of the transgenic pig is suppressed in immune rejection response during organ xenotransplantation.

10. The transgenic pig according to claim 9, wherein the organ is an islet.

11. A somatic donor cell line for the production of the transgenic pig of claim 7, which is introduced with a gene coding for human HO-1 (Heme oxygenase-1) protein and a gene coding for human TNFR1-Fc (Tumor necrosis factor receptor 1-Fc) fusion protein.

12. The somatic donor cell line according to claim 11, wherein the somatic donor cell line has Accession No. KCLRF-BP-00225.

13. A method for producing transplantable organs suppressed in immune rejection response, comprising:
   producing a transgenic pig by the method of claim 1; and
   isolating the organ from the transgenic pig.

14. The method according to claim 13, wherein the organ is an islet.

15. The method according to claim 13, wherein the organ shows decreased immune rejection response compared to the organ obtained from the pig genetically not modified.

16. A method for producing transplantable organs suppressed in immune rejection response, comprising:
   producing a transgenic pig by the method of claim 6; and
   isolating the organ from the transgenic pig.

17. The method according to claim 16, wherein the organ is an islet.

* * * * *